US012686663B2

(12) United States Patent
Aotsu et al.

(10) Patent No.: US 12,686,663 B2

(45) Date of Patent: Jul. 21, 2026

(54) FLUORINE-CONTAINING PYRAZOLE COMPOUND AND PRODUCTION METHOD THEREFOR

(71) Applicant: UNIMATEC CO., LTD., Tokyo (JP)

(72) Inventors: Rie Aotsu, Kitaibaraki (JP); Junya Seino, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 401 days.

(21) Appl. No.: 18/287,442

(22) PCT Filed: Mar. 31, 2022

(86) PCT No.: PCT/JP2022/016469

§ 371 (c)(1),
(2) Date: Oct. 18, 2023

(87) PCT Pub. No.: WO2022/230599

PCT Pub. Date: Nov. 3, 2022

(65) Prior Publication Data

US 2024/0217934 A1 Jul. 4, 2024

(30) Foreign Application Priority Data

Apr. 27, 2021 (JP) ................................ 2021-075090

(51) Int. Cl.
*C07D 231/22* (2006.01)

(52) U.S. Cl.
CPC .................................. *C07D 231/22* (2013.01)

(58) Field of Classification Search
None
See application file for complete search history.

(56) References Cited

U.S. PATENT DOCUMENTS

| | | | | |
|---|---|---|---|---|
| 2004/0072692 | A1 | 4/2004 | Hoffmann et al. | |
| 2006/0122063 | A1 | 6/2006 | Hoffmann et al. | |
| 2010/0016612 | A1 | 1/2010 | Umetani et al. | |
| 2015/0152062 | A1 | 6/2015 | Pazenok et al. | |
| 2015/0203511 | A1 | 7/2015 | Arimori et al. | |
| 2015/0223460 | A1 | 8/2015 | Arimori et al. | |
| 2016/0183529 | A1 | 6/2016 | Arimori et al. | |
| 2016/0289213 | A1 | 10/2016 | Pazenok et al. | |
| 2016/0340340 | A1 | 11/2016 | Sharpe et al. | |
| 2019/0359597 | A1* | 11/2019 | Allen | A61K 31/4178 |
| 2021/0403455 | A1 | 12/2021 | Seino et al. | |
| 2024/0116915 | A1 | 4/2024 | Seino et al. | |

FOREIGN PATENT DOCUMENTS

| | | | | |
|---|---|---|---|---|
| CN | 101627015 | A | 1/2010 | |
| CN | 104470900 | A | 3/2015 | |
| EP | 3860636 | A1 | 8/2021 | |
| JP | H05-230029 | A | 9/1993 | |
| JP | 2015-27978 | A | 2/2015 | |
| JP | 2016-539945 | A | 12/2016 | |
| JP | 2020-079269 | A | 5/2020 | |
| WO | 2004-013131 | A2 | 2/2004 | |
| WO | 2014-051161 | A1 | 4/2014 | |
| WO | 2015-089003 | A1 | 6/2015 | |
| WO | 2020-072580 | A1 | 4/2020 | |
| WO | 2020-116296 | A1 | 6/2020 | |
| WO | WO-2021095577 | A1 * | 5/2021 | C07D 417/04 |

OTHER PUBLICATIONS

Machine Translation of WO 2021/095577 A1, Translated by Patent Translate Espacenet.org on Jan. 20, 26, 62 pages (Year: 2021).*

Mwangi et al. "Removal of Fluoride lons in Stored Drinking Water by Triethylamine Chemically Modified Polyethylene Containers" International Journal 2019, 13, 175-184. DOI: 10.1007/s41742-018-0163-2 (Year: 2019).*

Barriero et al. "The Methylation Effect in Medicinal Chemistry" Chemical Reviews 2011, 111, 5215-5246. DOI: 10.1021/cr200060g ( Year: 2011).*

Meanwell, N. A. "The Influence of Bioisosteres in Drug Design: Tactical Applications to Address Developability Problems" Top Med Chem 2015, 9, Select Pages. DOI: 10.1007/7355_2013_29 (Year: 2015).*

Bargamova et. al. "5-Fluoro-substituted pyrazoles" Izvestiya Akademii Nauk SSSR, Seriya Khimicheskaya, 1990 vol. 11, pp. 2583-2589. ISSN: 0002-3352. (Year: 1990).*

First Office Action issued in corresponding India Patent Application No. 202337077357 dated Mar. 20, 2025, with English translation (7 Pages).

Extended European Search Report for corresponding European Patent Application No. 22795515.0 dated Jun. 17, 2025 (10 Pages).

Chi Ki-Whan. "Synthesis of fluorinated N-arylpyrazoles with perfluoro-2-methyl-2-pentene and arylhydrazines" Journal of Fluorine Chemistry, vol. 98, Issue 1, Aug. 10, 1999, pp. 29-36. DOI: 10.1016/S0022-1139(99)00079-2. Abstract Only.

(Continued)

*Primary Examiner* — Jennifer A Berrios
*Assistant Examiner* — Sophia Reilly
(74) *Attorney, Agent, or Firm* — Harness, Dickey & Pierce, P.L.C.

(57) ABSTRACT

A fluorine-containing pyrazole compound represented by the following general formula (1):

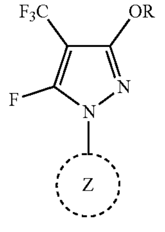

(1)

wherein in the general formula (1) above, R represents a hydrocarbon group having 1 to 12 carbon atoms; and a ring Z represents a phenyl group having a substituent, or a condensed ring containing no heteroatom as a ring atom.

10 Claims, No Drawings

(56) References Cited

OTHER PUBLICATIONS

International Search Report for corresponding International Application No. PCT/JP2022/016469 dated Jun. 14, 2022, with English translation (7 Pages).
Written Opinion for corresponding International Application No. PCT/JP2022/016469 dated Jun. 14, 2022, with English translation (8 Pages).
International Preliminary Report on Patentability for corresponding International Application No. PCT/JP2022/016469 dated Jun. 14, 2022, with English translation (9 Pages).
Notice of Reasons for Refusal for corresponding Japanese Patent Application No. 2023-517214 dated Aug. 19, 2024, with English translation (7 Pages).
Office Action for corresponding Indian Patent Application No. 202337077357 dated Dec. 10, 2025 (10 Pages).
First Office Action for corresponding Chinese Patent Application No. 202280029863.4 dated May 25, 2026, with English translation (24 Pages).

* cited by examiner

FLUORINE-CONTAINING PYRAZOLE COMPOUND AND PRODUCTION METHOD THEREFOR

CROSS REFERENCE TO RELATED APPLICATIONS

The present application is a national stage application of International Patent Application No. PCT/JP2022/016469 filed on Mar. 31, 2022, which claims the benefit of Japanese Patent Application No. 2021-075090, filed on Apr. 27, 2021. The contents of the above applications are incorporated herein by reference in their entirety.

BACKGROUND

Technical Field

The present disclosure relates to a fluorine-containing pyrazole compound and production method therefor.

Related Art

Conventionally, fluorine-containing pyrazole compounds have been reported to have various biological activities. Among them, a compound having a ring structure having no heteroatom serving as a ring atom, as a substituent at the 1-position of a pyrazole ring and substituents at the 3- and 5-positions of the pyrazole ring is expected to be used in the fields of medicine and agrochemicals.

More specifically, International Publication No. WO 2014/051161 reports that a compound having a 1-phenyl-pyrazole structure has an antibacterial activity against rice blast, wheat rust disease, and the like. International Publication No. WO 2015/089003 reports that a compound having a 1-phenyl-pyrazole structure has a herbicidal activity against white goosefoot, Indian mallow, and the like. International Publication No. WO 2020/072580 reports that a compound having a 1-phenyl-pyrazole structure has an inhibitory activity of matriptase 2 which relates to hepcidin suppression.

Therefore, with an expectation of improving useful activities such as biological activity, a compound having a substituent composed of a ring structure having no heteroatom as a ring atom at the 1-position of a pyrazole ring, substituents at the 3-position and the 5-position of the pyrazole ring, and further a trifluoromethyl group at the 4-position of the pyrazole ring, has been drawing attraction in development thereof.

For the compound having a substituent composed of a ring structure having no heteroatom as a ring atom at the 1-position of the pyrazole ring and substituents at the 3- and 5-positions of the pyrazole ring, reactivity and reaction selectivity of a substrate need to be strictly controlled in order to further introduce a trifluoromethyl group at the 4-position of the pyrazole ring, and no production examples of such a compound have been reported so far. Therefore, a fluorine-containing pyrazole compound having a substituent composed of a ring structure having no heteroatom as a ring atom at the 1-position, substituents at the 3- and 5-positions, and further a trifluoromethyl group at the 4-position has been waited for further development.

Therefore, the present inventors have discovered that a reaction with a specific raw material enables introduction of a substituent composed of a specific ring structure having no heteroatom as a ring atom at the 1-position of a pyrazole ring, a trifluoromethyl group at the 4-position of the pyrazole ring, and specific substituents at the 3-position and the 5-position of the pyrazole ring, and thus have completed the present disclosure. Namely, the present disclosure provides a novel fluorine-containing pyrazole compound having a substituent composed of a specific ring structure having no heteroatom as a ring atom at the 1-position, a trifluoromethyl group at the 4-position, and specific substituents at the 3-position and the 5-position, which have not been known conventionally, and a production method capable of easily producing the fluorine-containing pyrazole compound.

SUMMARY

The configuration of the present disclosure is as follows.

[1] A fluorine-containing pyrazole compound represented by the following general formula (1):

[Formula 1]

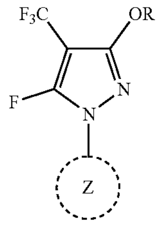

(1)

wherein R represents a hydrocarbon group having 1 to 12 carbon atoms; and a ring Z represents a phenyl group having a substituent, or a condensed ring containing no heteroatom as a ring atom.

[2] The fluorine-containing pyrazole compound according to [1], wherein a number of $\pi$ electrons constituting the ring Z is 6, 10, 14, 18 or 22.

[3] A method for producing a fluorine-containing pyrazole compound, including reacting a fluoroisobutylene derivative represented by the following general formula (2) with a compound represented by the following general formula (3) or a salt thereof to obtain a fluorine-containing pyrazole compound represented by the following general formula (1):

[Formula 2]

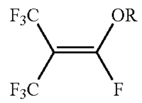

(2)

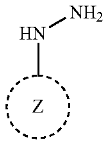

(3)

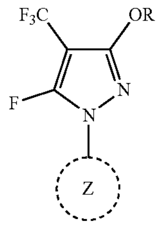

(1)

wherein

R represents a hydrocarbon group having 1 to 12 carbon atoms; and a ring Z represents a phenyl group having a substituent, or a condensed ring containing no heteroatom as a ring atom.

[4] A method for producing a fluorine-containing pyrazole compound, including reacting a fluoroisobutane derivative represented by the following general formula (4) with a compound represented by the following general formula (3) or a salt thereof to obtain a fluorine-containing pyrazole compound represented by the following general formula (1):

[Formula 3]

(4)

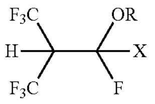

(3)

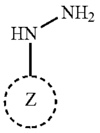

(1)

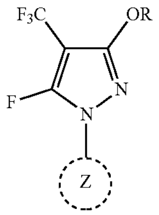

wherein

R represents a hydrocarbon group having 1 to 12 carbon atoms,

X represents a halogen atom, —$OA^1$, —$SO_mA^1$ where m is an integer of 0 to 3, or —$NA^1A^2$, $A^1$ and $A^2$ each independently represent a hydrogen atom or a hydrocarbon group having 1 to 10 carbon atoms, and a ring Z represents a phenyl group having a substituent, or a condensed ring containing no heteroatom as a ring atom.

[5] The method for producing a fluorine-containing pyrazole compound according to [3], wherein a step of obtaining a fluorine-containing pyrazole compound is carried out in the presence of a fluoride ion scavenger.

[6] The method for producing a fluorine-containing pyrazole compound according to [3], wherein a number of π electrons constituting the ring Z is 6, 10, 14, 18 or 22.

[7] The method for producing a fluorine-containing pyrazole compound according to [4], wherein a step of obtaining a fluorine-containing pyrazole compound is carried out in the presence of a fluoride ion scavenger.

[8] The method for producing a fluorine-containing pyrazole compound according to [4], wherein a number of π electrons constituting the ring Z is 6, 10, 14, 18 or 22.

[9] The method for producing a fluorine-containing pyrazole compound according to [5], wherein a number of π electrons constituting the ring Z is 6, 10, 14, 18 or 22.

[10] The method for producing a fluorine-containing pyrazole compound according to [7], wherein a number of π electrons constituting the ring Z is 6, 10, 14, 18 or 22.

Effects of Disclosure

A novel fluorine-containing pyrazole compound having a substituent composed of a specific ring structure having no heteroatom as a ring atom at the 1-position, a trifluoromethyl group at the 4-position, and specific substituents at the 3-position and the 5-position, and a production method capable of easily producing the fluorine-containing pyrazole compound, can be provided.

DETAILED DESCRIPTION (Fluorine-Containing Pyrazole Compound)

The fluorine-containing pyrazole compound of the present disclosure is represented by the following general formula (1):

[Formula 4]

(1)

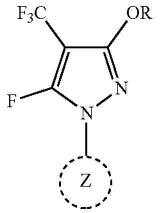

wherein in the general formula (1) above,

R represents a hydrocarbon group having 1 to 12 carbon atoms, and a ring Z represents a phenyl group having a substituent, or a condensed ring containing no heteroatom as a ring atom.

The fluorine-containing pyrazole compound of the present disclosure has a group Z of a phenyl group having a substituent or a condensed ring (for example, a polycyclic aromatic hydrocarbon) containing no heteroatom such as N (nitrogen), S (sulfur), or O (oxygen) as a ring atom constituting a ring structure on the 1-position of a pyrazole ring, and specific substituents (—OR, —$CF_3$, —F) on the 3-position, 4-position, and 5-position of the pyrazole ring, and thereby it can have an excellent effect from the viewpoint of structural expandability. In particular, desired biological activities (for example, hormone or enzyme inhibitory activity, bactericidal activity, insecticidal activity, and herbicidal activity) can be expected. The condensed ring (for example, a polycyclic aromatic hydrocarbon) Z containing no heteroatom as a ring atom located on the 1-position of a pyrazole ring may or may not further have a substituent. The ring Z can impart desired properties to the fluorine-containing pyrazole compound depending on a size of the ring, the number of ring atoms, the number of π electrons constituting the ring Z, as well as the number, type and presence or absence of substituents or the like. Moreover, the substituents on the 3- and 5-positions of the pyrazole ring being different groups (—OR and —F) facilitates derivatization into an asymmetric structure by elimination or reaction of these groups, which can be expected to be used as an intermediate. More specifically, a fluorine-containing pyrazole compound being reacted under acidic conditions to modify —OR enables to form a derivative. Moreover, a fluorine-containing pyrazole compound being reacted under basic conditions to modify —F enables to form a derivative. The fluorine-containing pyrazole compound of one embodiment is useful in the field of electronic materials such as organic semiconductors and liquid crystals.

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12 and may be a branched chain hydrocarbon group or a chain hydrocarbon group having no branch. The aromatic hydrocarbon group is not particularly limited as long as the total number of carbon atoms is 5 to 12 and may even be an aromatic hydrocarbon group having a substituent or an aromatic hydrocarbon group having no substituent. Moreover, the aromatic hydrocarbon group may have a condensed polycyclic structure. The alicyclic hydrocarbon group is not particularly limited as long as the total number of carbon atoms is 3 to 12 and may even be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, an n-propyl group, an i-propyl group, a n-butyl group, an i-butyl group, a sec-butyl group, a t-butyl group, a pentyl group, a hexyl group, a heptyl group, an octyl group, a nonyl group, a decyl group, an undecyl group, a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group, a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group, a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group, a norbornyl group and the like.

R is preferably an alkyl group having 1 to 10 carbon atoms. R being an alkyl group having 1 to 10 carbon atoms can easily prepare the fluoroisobutylene derivative of the general formula (2) and the fluoroisobutane derivative of the general formula (4), which are raw materials of the fluorine-containing pyrazole compound.

The ring Z may be a phenyl group having a substituent of a monocyclic structure or a group composed of a condensed ring structure containing no heteroatom as a ring atom.

Typically, the number of π electrons constituting the ring Z is 4n+2 (n is a positive integer), but the number of π electrons is preferably 6, 10, 14, 18 or 22. The number of π electrons constituting the ring Z is more preferably 6 or 10. When the ring Z has the aforementioned structure, polarity and planarity of the fluorine-containing pyrazole compound are controlled, so that dynamics are improved and more effective biological activity can be imparted.

More specifically, a group composed of ring Z includes a phenyl group having a substituent, a naphthyl group, a chloronaphthyl group, a bromonaphthyl group, a methoxynaphthyl group, a dihydroacenaphthyl group, an anthracenyl group, a phenanthryl group, a phenalenyl group, a pyrenyl group, a triphenylenyl group, a tetracenyl group, a chrysenyl group, a benz[a]anthracenyl group, a benzo[c]phenanthryl group, a perylenyl group, a pentacenyl group, a benzo[a]pyrenyl group, a benzo[e]pyrenyl group, a benzo[a]tetracenyl group, a corannulenyl group, a pentacenyl group, a picenyl group, a dibenzo[a,j]anthracenyl group and the like. Among these groups, the group composed of ring Z is preferably a phenyl group having a substituent, a naphthyl group, a naphthyl group having a substituent, a dihydroacenaphthyl group, or a phenanthryl group. Additionally, when the ring Z is a condensed ring containing no heteroatom as a ring atom, a substituent may or may not be further bonded to the ring atom in the group composed of ring Z. When the ring Z is a condensed ring containing no heteroatom as a ring atom, the substituent of ring Z may or may not have a heteroatom, and examples of the substituent include halogen atoms such as Cl and Br, alkyl groups, alkoxy groups such as OMe, and halogenated alkyl groups such as $CF_3$. When the ring Z is a phenyl group having a substituent, the number of the substituent is not particularly limited as long as it is 1 to 5, and examples of the substituent include halogen atoms such as F, Cl, Br, and I, alkyl groups such as a methyl group, halogenated alkyl groups such as $CF_3$, nitro groups, alkoxy groups such as OMe, halogenated alkoxy groups such as $OCF_3$, and sulfonyl groups.

(Method for Producing Fluorine-Containing Pyrazole Compound)

The method for producing a fluorine-containing pyrazole compound according to one embodiment includes (a) reacting a fluoroisobutylene derivative represented by the following general formula (2) with a compound represented by the following general formula (3) or a salt thereof to obtain a fluorine-containing pyrazole compound represented by the following general formula (1):

[Formula 5]

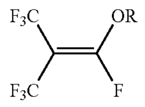

(2)

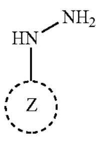

(3)

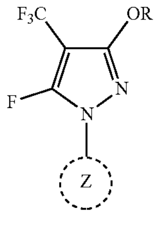

(1)

wherein in the general formulae (1) to (3) above,

R represents a hydrocarbon group having 1 to 12 carbon atoms; and a ring Z represents a phenyl group having a substituent, or a condensed ring containing no heteroatom as a ring atom.

Preferably, the above (a) obtaining the fluorine-containing pyrazole compound is preferably carried out in the presence of a fluoride ion scavenger. Namely, the fluoroisobutylene derivative represented by the general formula (2) is preferably reacted with the compound represented by the general formula (3) or a salt thereof in the presence of the fluoride ion scavenger. The fluoride ion scavenger is not particularly limited as long as it is a substance having a function of capturing fluorine ions, and examples of the fluoride ion scavenger include lithium, sodium, magnesium, potassium, calcium, tetramethylammonium, trifluoroacetic acid, heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonylimide, tetraphenylboric acid, tetrakis[3,5-bis(trifluoromethyl)phenyl]boric acid, tetrakis(pentafluorophenyl)borate. A cation derived from the fluoride ion scavenger captures fluorine ions free from the fluoroisobutylene derivative represented by the general formula (2) during reaction, allowing a salt having low solubility to precipitate in an organic solvent to promote a reaction, and enabling to obtain the fluorine-containing pyrazole compound represented by the general formula (1) above in a high yield.

In the aforementioned general formulae (1) and (3), the number of π electrons constituting the ring Z is preferably 6, 10, 14, 18, or 22. Moreover, R in the general formulae (1) and (2) above preferably represents an alkyl group having 1 to 10 carbon atoms.

A reaction of (a) above between the fluoroisobutylene derivative represented by the general formula (2) and the compound represented by the general formula (3) is represented by the following reaction formula (A).

[Formula 6]

(A)

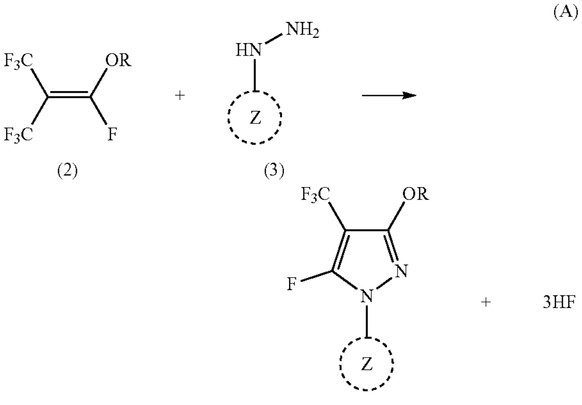

(2) (3) (1)

In the reaction formula (A), the compound of the general formula (3) each may be in a form of salt. The form of salt includes a form of at least one moiety of the amino moiety ($—NH_2$) and the imino moiety ($=NH$) constituting the amidino group of the compound of the general formula (3), being cationized to ($—NH_3^+$) and ($=NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrazole compound according to one embodiment, for example, reaction (a) above can be carried out in one step in the presence of the hydrogen halide scavenger. Therefore, the fluorine-containing pyrazole compound of the general formula (1) above can be easily obtained. Incidentally, the reaction of (a) above forms a cyclic pyrazole structure between the fluoroisobutylene derivative and the amidino group of the compound of the general formula (3). At the 1-position of the pyrazole structure, a group derived from the ring structure Z of the compound of the general formula (3) is located. Further, —OR, $CF_3$, and F derived from the fluoroisobutylene derivative are located at the 3-position, 4-position, and 5-position of the pyrazole structure, respectively.

The hydrogen halide scavenger is a substance having a function of capturing hydrogen fluoride (HF) formed from a hydrogen atom derived from the amidino group in the compound of the general formula (3) and a fluorine atom derived from the fluoroisobutylene derivative of the general formula (2) in reaction formula (A) above. The hydrogen halide scavenger that is sodium hydroxide, potassium hydroxide, calcium hydroxide, sodium carbonate, potassium carbonate, sodium fluoride and potassium fluoride, and organic nitrogen derivatives such as pyridine, triethylamine, diisopropylethylamine, diazabicyclo nonane and diazabicyclo undecene, methyl triazabicyclodecene, diazabicyclo octane, and phosphazene base, can be used.

A reaction temperature upon reaction of (a) above is preferably 0 to 100° C., more preferably 5 to 50° ° C., and still more preferably 10 to 20° C. A reaction time upon reaction of (a) above is preferably 1 to 48 hours, more preferably 2 to 36 hours, and still more preferably 4 to 24 hours.

A solvent used in reaction (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water, and a water-insoluble solvent such as dichloromethane, toluene and diethyl ether. Moreover, as a catalyst for reaction of (a) above, quaternary ammonium halides such as benzyltriethylammonium chloride, a quaternary phosphonium halide, and crown ether, can be used.

The method for producing a fluorine-containing pyrazole compound according to another embodiment includes (b) reacting a fluoroisobutane derivative represented by the following general formula (4) with a compound represented by the following general formula (3) or a salt thereof to obtain a fluorine-containing pyrazole compound represented by the following general formula (1):

[Formula 7]

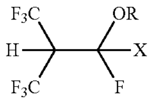

(4)

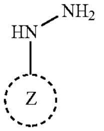

(3)

-continued (1)

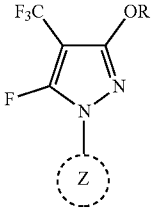

wherein in the general formulae (1), (3), and (4) above,

R represents a hydrocarbon group having 1 to 12 carbon atoms,

X represents a halogen atom, $—OA^1$, $—SO_mA^1$ where m is an integer of 0 to 3, or $—NA^1A^2$, $A^1$ and $A^2$ each independently represent a hydrogen atom or a hydrocarbon group having 1 to 10 carbon atoms, and a ring Z represents a phenyl group having a substituent, or a condensed ring containing no heteroatom as a ring atom.

Preferably, the above (b) obtaining the fluorine-containing pyrazole compound is preferably carried out in the presence of a fluoride ion scavenger. The fluoroisobutane derivative represented by the general formula (4) is preferably reacted with the compound represented by the general formula (3) or a salt thereof in the presence of a fluoride ion scavenger. The fluoride ion scavenger is not particularly limited as long as it is a substance having a function of capturing fluorine ions, and examples of the fluoride ion scavenger include lithium, sodium, magnesium, potassium, calcium, tetramethylammonium, trifluoroacetic acid, and heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonylimide, tetraphenylboric acid, tetrakis[3,5-bis(trifluoromethyl)phenyl]boric acid, tetrakis(pentafluorophenyl)borate. A cation derived from the fluoride ion scavenger captures a fluorine ion free from the fluoroisobutane derivative represented by the general formula (4) during reaction, allowing a salt having low solubility to precipitate in an organic solvent to promote a reaction, and enabling to obtain the fluorine-containing pyrazole compound represented by the aforementioned general formula (1) in a high yield.

In the aforementioned general formulae (1) and (3), the number of π electrons constituting the ring Z is preferably 6, 10, 14, 18, or 22. Moreover, R in the aforementioned general formulae (1) and (4) preferably represents an alkyl group having 1 to 10 carbon atoms.

The reaction of (b) above between the fluoroisobutane derivative represented by the general formula (4) and the compound represented by the general formula (3) is represented by the following reaction formula (B).

[Formula 8]

(B)

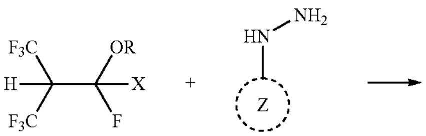

(4) (3)

-continued

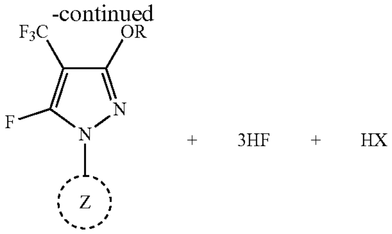

(1)

In the aforementioned reaction formula (B), the compounds of the general formula (3) each may be in a form of salt. The form of salt includes a form of at least one moiety of the amino moiety ($—NH_2$) and the imino moiety ($=NH$) constituting the amidino group of the compound of the general formula (3), being cationized to ($—NH_3^+$) and ($=NH_2^+$) to form a salt with the counterion. The counterion is not particularly limited as long as it is a monovalent anion, and includes, for example, halide ions such as $F^-$, $Cl^-$, $Br^-$, and $I^-$.

Examples of the halogen atom that is X include F, Cl, Br, and I. $A^1$ included in $—OA^1$ and $—SO_mA^1$ where m is an integer of 0 to 3, that are X, represents a hydrogen atom or a hydrocarbon group having 1 to 10 carbon atoms. $A^1$ and $A^2$ included in $—NA^1A^2$, which are X, each independently represent a hydrogen atom or a hydrocarbon group having 1 to 10 carbon atoms. $A^1$ and $A^2$ representing a hydrocarbon group having 1 to 10 carbon atoms, can be, for example, hydrocarbon groups having 1 to 10 carbon atoms in the above R.

In the method for producing the fluorine-containing pyrazole compound according to the other embodiment, for example, the reaction of (B) above can be carried out in one step. Therefore, the fluorine-containing pyrazole compound of the general formula (1) above can be easily obtained. Incidentally, the reaction of (b) above forms a cyclic pyrazole structure between the fluoroisobutane derivative (4) and the amidino group of the compound of the general formula (3). At the 1-position of the pyrazole structure, a group derived from the ring structure Z of the compound of the general formula (3) is located. Further, —OR, $CF_3$, and F derived from the fluoroisobutane derivative are located at the 3-position, 4-position, and 5-position of the pyrazole structure, respectively.

A reaction temperature upon reaction of (b) above is preferably 0 to 100° C., more preferably 5 to 50° C., and still more preferably 10 to 20° C. A reaction time upon reaction of (b) above is preferably 1 to 48 hours, more preferably 2 to 36 hours, and still more preferably 4 to 24 hours. In the reaction of (b) above, the same hydrogen halide scavenger as (a) above can be used.

A solvent used in reaction (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for reaction (b) above, quaternary ammonium halides such as benzyltriethylammonium chloride, a quaternary phosphonium halide, crown ether and the like, can be used.

Although the embodiments of the present disclosure have been described above, the present disclosure is not limited to the aforementioned embodiments, and includes all aspects included in the concept and claims of the present disclosure and can be modified within the scope of the present disclosure.

EXAMPLES

Next, in order to further clarify the effect of the present disclosure, Examples will be described, but the present disclosure is not limited to these Examples.

Example 1

Production of 5-fluoro-3-methoxy-1-(9-phenanthryl)-4-trifluoromethylpyrazole In 10 ml of THF (tetrahydrofuran), 0.3 g (1.0 mmol) of 9-phenanthrylhydrazine hydrochloride and 0.3 g (1.4 mmol) of 1,3,3,3-tetrafluoro-1-methoxy-2-trifluoromethyl-1-propene were dissolved, and 0.6 g (3.9 mmol) of 1,8-diazabicyclo[5.4.0]undec-7-ene (hereinafter, sometimes referred to as "DBU") was added dropwise. The mixture was stirred at room temperature for about 64.3 hours, and then, the reaction solution was purified by a column to isolate 0.3 g (0.9 mmol) of 5-fluoro-3-methoxy-1-(9-phenanthryl)-4-trifluoromethylpyrazole represented by the following formula (C). The isolated yield of 5-fluoro-3-methoxy-1-(9-phenanthryl)-4-trifluoromethylpyrazole was 2.5%.

[Formula 9]

(C)

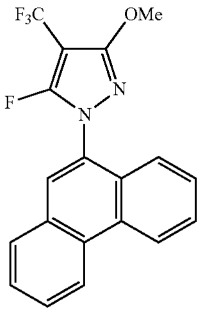

The analysis results of the target product obtained are as follows.

Mass Spectrum (APCI, m/z): 360.4 ([M]$^+$)

$^1$H-NMR (300 MHz, $CDCl_3$) δ ppm: 8.77 (d, 8.3 Hz, 1H), 8.74 (d, J=8.3 Hz, 1H), 7.95 (dd, J=7.3, 0.6 Hz, 1H), 7.86 (s, 1H), 7.74-7.80 (m, 2H), 7.66-7.70 (m, 3H), 4.02 (s, 3H)

Example 2

Production of 5-fluoro-3-methoxy-1-[2,6-dichloro-4-(trifluoromethyl)phenyl]-4-trifluoromethylpyrazole In 12 ml of acetonitrile, 0.5 g (2.1 mmol) of 2,6-dichloro-4-(trifluoromethyl)phenylhydrazine was dissolved, and 2.1 g (6.1 mmol) of sodium tetraphenylborate, 0.5 g (2.4 mmol) of 1,3,3,3-tetrafluoro-1-methoxy-2-(trifluoromethyl)-1-propene and 0.9 g (5.9 mmol) of DBU were added, the mixture was stirred at room temperature for 88 hours, and then the reaction solution was purified by a column to obtain a trace amount of a crude product of 0.3 g (0.9 mmol) of 5-fluoro-3-methoxy-1-[2,6-dichloro-4-(trifluoromethyl)phenyl]-4-trifluoromethylpyrazole represented by the following formula (D).

[Formula 10]

(D)

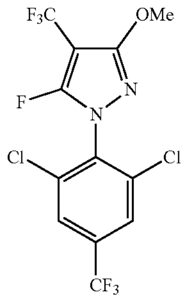

The analysis results of the target product obtained are as follows.

Mass Spectrum (APCI, m/z): 396.7 ([M]$^+$)

$^{19}$F-NMR (400 MHZ, $CDCl_3$) δ ppm: −59.5 (d, 3F), −108.4 (dd, 1F)

Example 3

Production of 5-fluoro-3-methoxy-1-(9-phenanthryl)-4-trifluoromethylpyrazole by Using 1,1,1,3,3-pentafluoro-3-methoxy-2-(trifluoromethyl)-propane instead of 1,3,3,3-tetrafluoro-1-methoxy-2-(trifluoromethyl)-1-propene of Example 1

In 10 ml of THF (tetrahydrofuran), 0.3 g (1.0 mmol) of 9-phenanthrylhydrazine hydrochloride and 0.3 g (1.4 mmol) of 1,1,1,3,3-pentafluoro-3-methoxy-2-(trifluoromethyl)-propane were dissolved, and 0.6 g (3.9 mmol) of 1,8-diazabicyclo[5.4.0]undec-7-ene was added dropwise. The mixture was stirred at room temperature for about 64.3 hours. Then, the analysis results of the obtained compound were the same as those of the product of Example 1.

Example 4

Production of 5-fluoro-3-methoxy-1-[2,6-dichloro-4-(trifluoromethyl)phenyl]-4-trifluoromethylpyrazole by Using 1,1,1,3,3-pentafluoro-3-methoxy-2-(trifluoromethyl)-propane instead of 1,3,3,3-tetrafluoro-1-methoxy-2-(trifluoromethyl)-1-propene of Example 2

In 12 ml of acetonitrile, 0.5 g (2.1 mmol) of 2,6-dichloro-4-(trifluoromethyl)phenylhydrazine was dissolved, and 2.1 g (6.1 mmol) of sodium tetraphenylborate, 0.6 g (2.4 mmol) of 1,1,1,3,3-pentafluoro-3-methoxy-2-(trifluoromethyl)-propane and 0.9 g (5.9 mmol) of DBU were added, and the mixture was stirred at room temperature for 88 hours. Then, the analysis results of the obtained compound were the same as those of the product of Example 2.

Example 5

Production of 5-fluoro-3-methoxy-1-(1-naphthyl)-4-trifluoromethylpyrazole

In 26 ml of tetrahydrofuran, 0.5 g (2.6 mmol) of 1-naphthylhydrazine hydrochloride was dissolved, and 0.6 g (2.8 mmol) of 1,3,3,3-tetrafluoro-1-methoxy-2-(trifluoromethyl)-1-propene and 1.6 g (10.5 mmol) of DBU were added, the mixture was stirred at room temperature for 64.3 hours, and then, the reaction solution was purified by a column to obtain 0.005 g of a crude purified product of 5-fluoro-3-methoxy-1-(1-naphthyl)-4-trifluoromethylpyrazole represented by the following formula (E).

[Formula 11]

(E)

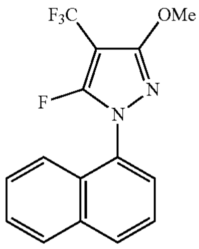

The analysis results of the target product obtained are as follows.

Mass Spectrum (APCI, m/z): 311.6 ($[M+H]^+$)

$^{19}$F-NMR (400 MHZ, $CDCl_3$) δ ppm: −58.07 (d, J=10.1 Hz, 3F), −120.47 (q, J=10.1 Hz, 1F)

Example 6

Production of 5-fluoro-3-methoxy-1-(4-bromo-1-naphthyl)-4-trifluoromethylpyrazole In 18 ml of tetrahydrofuran, 0.5 g (1.8 mmol) of (4-bromo-1-naphthyl)hydrazine hydrochloride was dissolved, and 0.4 g (1.9 mmol) of 1,3,3,3-tetrafluoro-1-methoxy-2-(trifluoromethyl)-1-propene and 1.1 g (7.2 mmol) of DBU were added, the mixture was stirred at room temperature for 87.5 hours, and then, the reaction solution was purified by a column to obtain 0.01 g of a crude purified product of 5-fluoro-3-methoxy-1-(4-bromo-1-naphthyl)-4-trifluoromethylpyrazole represented by the following formula (F).

[Formula 12]

(F)

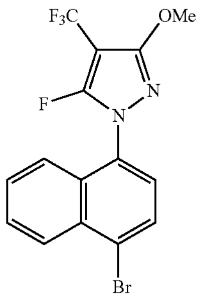

The analysis results of the target product obtained are as follows.

Mass Spectrum (APCI, m/z): 389.3 ($[M]^+$)

$^{19}$F-NMR (400 MHZ, $CDCl_3$) δ ppm: −58.15 (d, J=10.1 Hz, 3F), −120.16 (q, J=10.1 Hz, 1F)

Example 7

Production of 1-(4-chloro-1-naphthyl)-5-fluoro-3-methoxy-4-trifluoromethylpyrazole In 22 ml of tetrahydrofuran, 0.5 g (2.2 mmol) of (4-chloro-1-naphthyl)hydrazine hydrochloride was dissolved, and 0.5 g (2.4 mmol) of 1,3,3,3-tetrafluoro-1-methoxy-2-(trifluoromethyl)-1-propene and 1.3 g (8.5 mmol) of DBU were added, the mixture was stirred at room temperature for 88.9 hours, and then, the reaction solution was purified by a column to obtain 0.01 g of a crude purified product of 1-(4-chloro-1-naphthyl)-5-fluoro-3-methoxy-4-trifluoromethylpyrazole represented by the following formula (G).

[Formula 13]

(G)

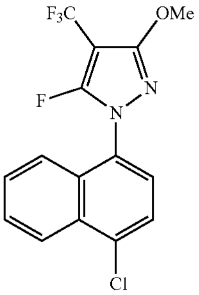

The analysis results of the target product obtained are as follows.

Mass Spectrum (APCI, m/z): 345.3 ($[M]^+$)

$^{19}$F-NMR (400 MHz, $CDCl_3$) δ ppm: −58.15 (d, J=10.1 Hz, 3F), −120.20 (q, J=10.1 Hz, 1F)

Example 8

Production of 1-(1,2-dihydroacenaphthylen-5-yl)-5-fluoro-3-methoxy-4-trifluoromethylpyrazole In 23 ml of tetrahydrofuran, 0.5 g (2.2 mmol) of (1,2-dihydroacenaphthylen-5-yl)hydrazine hydrochloride was dissolved, and 0.6 g (2.8 mmol) of 1,3,3,3-tetrafluoro-1-methoxy-2-(trifluoromethyl)-1-propene and 1.4 g (9.2 mmol) of DBU were added, the mixture was stirred at room temperature for 70.3 hours, and then, the reaction solution was purified by a column to obtain 0.03 g of a crude purified product of 1-(1,2-dihydroacenaphthylen-5-yl)-5-fluoro-3-methoxy-4-trifluoromethylpyrazole represented by the following formula (H).

[Formula 14]

(H)

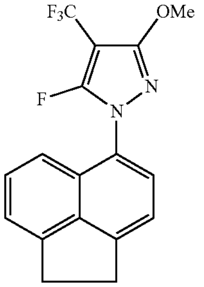

The analysis results of the target product obtained are as follows.

Mass Spectrum (APCI, m/z): 337.6 ($[M+H]^+$)

$^{19}$F-NMR (400 MHZ, $CDCl_3$) δ ppm: −58.00 (d, J=10.1 Hz, 3F), −120.82 (q, J=10.1 Hz, 1F)

Example 9

Production of 5-fluoro-3-methoxy-1-(2-naphthyl)-4-trifluoromethylpyrazole

In 26 ml of tetrahydrofuran, 0.5 g (2.6 mmol) of 2-naphthylhydrazine hydrochloride was dissolved, and 0.6 g (2.8 mmol) of 1,3,3,3-tetrafluoro-1-methoxy-2-(trifluoromethyl)-1-propene and 1.6 g (10.5 mmol) of DBU were added, the mixture was stirred at room temperature for 66.4 hours, and then, the reaction solution was purified by a column to obtain 0.01 g of a crude purified product of 5-fluoro-3-methoxy-1-(2-naphthyl)-4-trifluoromethylpyrazole represented by the following formula (I).

[Formula 15]

(I)

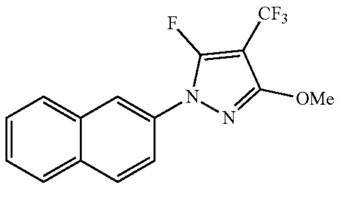

The analysis results of the target product obtained are as follows.

Mass Spectrum (APCI, m/z): 311.5 ($[M+H]^+$)

$^{19}$F-NMR (400 MHZ, $CDCl_3$) δ ppm: −58.25 (d, J=10.1 Hz, 3F), −120.43 (q, J=10.1 Hz, 1F)

Example 10

Production of 5-fluoro-3-methoxy-1-(6-methoxynaphthalen-2-yl)-4-trifluoromethylpyrazole In 19 ml of tetrahydrofuran, 0.5 g (1.9 mmol) of (6-methoxynaphthalen-2-yl)hydrazine hydrochloride was dissolved, and 0.5 g (2.4 mmol) of 1,3,3,3-tetrafluoro-1-methoxy-2-(trifluoromethyl)-1-propene and 1.2 g (7.9 mmol) of DBU were added, the mixture was stirred at room temperature for 71.3 hours, and then, the reaction solution was purified by a column to obtain 0.01 g (0.02 mmol) of 5-fluoro-3-methoxy-1-(6-methoxynaphthalen-2-yl)-4-trifluoromethylpyrazole represented by the following formula (J). The yield of 5-fluoro-3-methoxy-1-(6-methoxynaphthalen-2-yl)-4-trifluoromethylpyrazole was 1.2%.

[Formula 16]

(J)

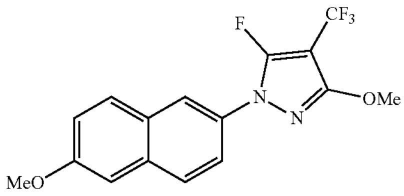

The analysis results of the target product obtained are as follows.

Mass Spectrum (APCI, m/z): 341.4 ($[M+H]^+$)

$^{19}$F-NMR (400 MHZ, $CDCl_3$) δ ppm: −58.17 (d, J=10.1 Hz, 3F), −120.92 (q, J=10.1 Hz, 1F)

Example 11

Production of 1-(6-bromonaphthalen-2-yl)-5-fluoro-3-methoxy-4-trifluoromethylpyrazole In 18 ml of tetrahydrofuran, 0.5 g (1.8 mmol) of (6-bromonaphthalen-2-yl)hydrazine hydrochloride was dissolved, and 0.4 g (1.9 mmol) of 1,3,3,3-tetrafluoro-1-methoxy-2-(trifluoromethyl)-1-propene and 1.1 g (7.2 mmol) of DBU were added, the mixture was stirred at room temperature for 64.4 hours, and then, the reaction solution was purified by a column to obtain 0.01 g of a crude purified product of 1-(6-bromonaphthalen-2-yl)-5-fluoro-3-methoxy-4-trifluoromethylpyrazole represented by the following formula (K).

[Formula 17]

(K)

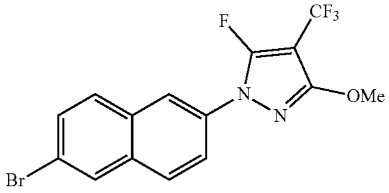

The analysis results of the target product obtained are as follows.

Mass Spectrum (APCI, m/z): 389.4 ($[M+H]^+$)

$^{19}$F-NMR (400 MHZ, $CDCl_3$) δ ppm: −58.32 (d, J=10.1 Hz, 3F), −120.13 (q, J=10.1 Hz, 1F)

Example 12

Production of 5-fluoro-1-(4-fluorophenyl)-3-methoxy-4-trifluoromethylpyrazole In 19.2 ml of tetrahydrofuran, 0.5 g (3.1 mmol) of 4-fluorophenylhydrazine hydrochloride was dissolved, and 3.0 g (9.2 mmol) of potassium bis(trifluoromethanesulfonyl) imido, 0.8 g (3.8 mmol) of 1,3,3,3-tetrafluoro-1-methoxy-2-(trifluoromethyl)-1-propene and 2.9 g (9.3 mmol) of phosphazene base $P_1$-t-Bu-tris(tetramethylene) were added, the mixture was stirred at room temperature for 69.5 hours, and then, the reaction solution was purified by a column to obtain a crude purified product of 5-fluoro-1-(4-fluorophenyl)-3-methoxy-4-trifluoromethylpyrazole represented by the following formula (L).

[Formula 18]

(L)

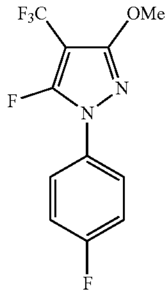

The analysis results of the target product obtained are as follows.

Mass Spectrum (APCI, m/z): 279.5 ($[M+H]^+$)

$^{19}$F-NMR (400 MHZ, $CDCl_3$) δ ppm: −58.31 (d, J=10.1 Hz, 3F), −114.55-−114.47 (m, 1H), −121.14 (q, J=10.1 Hz, 1F)

Example 13

Production of 1-(4-chlorophenyl)-5-fluoro-3-methoxy-4-trifluoromethylpyrazole In 28 ml of acetonitrile, 0.8 g (2.8 mmol) of p-chlorophenylhydrazine hydrochloride was dissolved, and 0.7 g (3.3 mmol) of 1,3,3,3-tetrafluoro-1-methoxy-2-(trifluoromethyl)-1-propene and 1.9 g (14.6 mmol) of N,N-diisopropylethylamine were added, the mixture was stirred at room temperature for 72.4 hours, and then, the reaction solution was purified by a column to obtain 0.02 g of a crude purified product of 1-(4-chlorophenyl)-5-fluoro-3-methoxy-4-trifluoromethylpyrazole represented by the following formula (M).

[Formula 19]

(M)

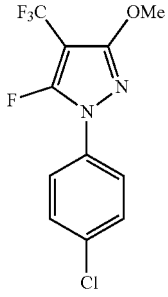

The analysis results of the target product obtained are as follows.

Mass Spectrum (APCI, m/z): 295.4 ($[M+H]^+$)

$^{19}$F-NMR (400 MHz, $CDCl_3$) δ ppm: −58.40 (d, J=10.1 Hz, 3F), −120.32 (q, J=10.1 Hz, 1F)

Example 14

Production of 1-(2,4-dichlorophenyl)-5-fluoro-3-methoxy-4-trifluoromethylpyrazole In 23 ml of acetonitrile, 0.8 g (2.4 mmol) of 2,4-dichlorophenylhydrazine hydrochloride was dissolved, and 0.6 g (2.8 mmol) of 1,3,3,3-tetrafluoro-1-methoxy-2-(trifluoromethyl)-1-propene and 1.6 g (12.3 mmol) of N,N-diisopropylethylamine were added, the mixture was stirred at room temperature for 63.3 hours, and then, the reaction solution was purified by a column to obtain 0.02 g of a crude purified product of 1-(2,4-dichlorophenyl)-5-fluoro-3-methoxy-4-trifluoromethylpyrazole represented by the following formula (N).

[Formula 20]

(N)

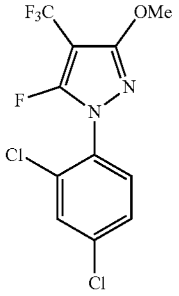

The analysis results of the target product obtained are as follows.

Mass Spectrum (APCI, m/z): 329.2 ($[M+H]^+$)

$^{19}$F-NMR (400 MHZ, $CDCl_3$) δ ppm: −58.41 (d, J=10.1 Hz, 3F), −118.40 (q, J=10.1 Hz, 1F)

Example 15

Production of 5-fluoro-3-methoxy-1-(4-methoxyphenyl)-4-trifluoromethylpyrazole In 29 ml of acetonitrile, 0.5 g (2.9 mmol) of 4-methoxyphenylhydrazine hydrochloride was dissolved, and 0.7 g (3.3 mmol) of 1,3,3,3-tetrafluoro-1-methoxy-2-(trifluoromethyl)-1-propene and 2.0 g (15.2 mmol) of N,N-diisopropylethylamine were added, the mixture was stirred at room temperature for 89.5 hours, and then, the reaction solution was purified by a column to obtain 0.1 g (0.3 mmol) of 5-fluoro-3-methoxy-1-(4-methoxyphenyl)-4-trifluoromethylpyrazole represented by the following formula (O). The yield of 5-fluoro-3-methoxy-1-(4-methoxyphenyl)-4-trifluoromethylpyrazole was 11.9%.

[Formula 21]

(O)

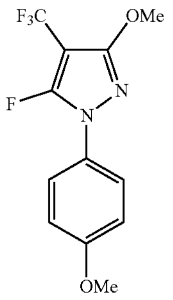

The analysis results of the target product obtained are as follows.

Mass Spectrum (APCI, m/z): 391.2 ($[M+H]^+$)

$^{19}F$-NMR (400 MHZ, $CDCl_3$) δ ppm: −58.17 (d, J=10.1 Hz, 3F), −121.85 (q, J=10.1 Hz, 1F)

Example 16

Production of 5-fluoro-3-methoxy-1-(4-nitrophenyl)-4-trifluoromethylpyrazole In 26 ml of acetonitrile, 0.5 g (2.7 mmol) of 4-nitrophenylhydrazine hydrochloride was dissolved, and 0.6 g (2.8 mmol) of 1,3,3,3-tetrafluoro-1-methoxy-2-(trifluoromethyl)-1-propene and 1.8 g (14.1 mmol) of N,N-diisopropylethylamine were added, the mixture was stirred at room temperature for 65.8 hours, and then, the reaction solution was purified by a column to obtain a crude purified product of 5-fluoro-3-methoxy-1-(4-nitrophenyl)-4-trifluoromethylpyrazole represented by the following formula (P)

[Formula 22]

(P)

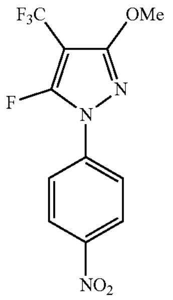

The analysis results of the target product obtained are as follows.

$^{19}F$-NMR (400 MHZ, $CDCl_3$) δ ppm: −58.72 (d, J=11.6 Hz, 3F), −117.87 (q, J=10.1 Hz, 1F)

Example 17

Production of 1-(4-bromophenyl)-5-fluoro-3-methoxy-4-trifluoromethylpyrazole In 22 ml of acetonitrile, 0.5 g (2.2 mmol) of 4-bromophenylhydrazine hydrochloride was dissolved, and 0.5 g (2.4 mmol) of 1,3,3,3-tetrafluoro-1-methoxy-2-(trifluoromethyl)-1-propene and 1.5 g (12.0 mmol) of N,N-diisopropylethylamine were added, the mixture was stirred at room temperature for 62.8 hours, and then, the reaction solution was purified by a column to obtain 0.05 g of a crude purified product of 1-(4-bromophenyl)-5-fluoro-3-methoxy-4-trifluoromethylpyrazole represented by the following formula (Q).

[Formula 23]

(Q)

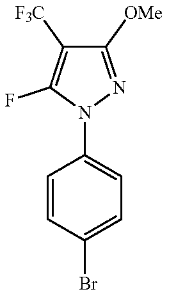

The analysis results of the target product obtained are as follows.

Mass Spectrum (APCI, m/z): 338.9 ($[M+H]^+$)

$^{19}F$-NMR (400 MHZ, $CDCl_3$) δ ppm: −58.42 (d, J=10.1 Hz, 3F), −120.17 (q, J=10.1 Hz, 1F)

Example 18

Production of 1-[4-(trifluoromethoxy)phenyl]-5-fluoro-3-methoxy-4-trifluoromethylpyrazole In 22 ml of acetonitrile, 0.5 g (2.2 mmol) of 4-(trifluoromethoxy)phenylhydrazine hydrochloride was dissolved, and 0.6 g (2.8 mmol) of 1,3,3,3-tetrafluoro-1-methoxy-2-(trifluoromethyl)-1-propene and 1.5 g (11.3 mmol) of N,N-diisopropylethylamine were added, the mixture was stirred at room temperature for 43.2 hours, and then, the reaction solution was purified by a column to obtain 0.05 g of a crude purified product of 1-[4-(trifluoromethoxy)phenyl]-5-fluoro-3-methoxy-4-trifluoromethylpyrazole represented by the following formula (R).

[Formula 24]

(R)

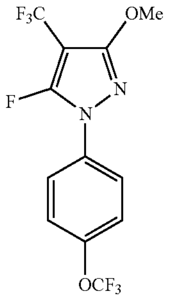

The analysis results of the target product obtained are as follows.

Mass Spectrum (APCI, m/z): 345.0 ($[M+H]^+$)

$^{19}F$-NMR (400 MHZ, $CDCl_3$) δ ppm: −58.42 (d, J=10.1 Hz, 3F), −59.21 (s, 3H), −120.47 (q, J=10.1 Hz, 1F)

Example 19

Production of 5-fluoro-3-methoxy-1-(4-methylphenyl)-4-trifluoromethylpyrazole

In 32 ml of acetonitrile, 0.5 g (3.2 mmol) of p-tolylhydrazine hydrochloride was dissolved, and 0.8 g (3.8 mmol) of 1,3,3,3-tetrafluoro-1-methoxy-2-(trifluoromethyl)-1-propene and 2.1 g (16.4 mmol) of N,N-diisopropylethylamine were added, the mixture was stirred at room temperature for 71.6 hours, and then, the reaction solution was purified by a column to obtain 0.01 g (0.04 mmol) of 5-fluoro-3-methoxy-1-(4-methylphenyl)-4-trifluoromethylpyrazole represented by the following formula (S). The yield of 5-fluoro-3-methoxy-1-(4-methylphenyl)-4-trifluoromethylpyrazole was 1.3%.

[Formula 25]

(S)

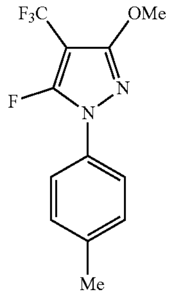

The analysis results of the target product obtained are as follows.

Mass Spectrum (APCI, m/z): 274.9 ($[M+H]^+$)

$^{19}$F-NMR (400 MHZ, $CDCl_3$) δ ppm: −58.21 (d, J=10.1 Hz, 3F), −120.20 (q, J=10.1 Hz, 1F)

Example 20

Production of 5-fluoro-1-(2,4-difluorophenyl)-3-methoxy-4-trifluoromethylpyrazole In 28 ml of acetonitrile, 0.5 g (2.8 mmol) of 2,4-difluorophenylhydrazine hydrochloride was dissolved, and 0.7 g (3.3 mmol) of 1,3,3,3-tetrafluoro-1-methoxy-2-(trifluoromethyl)-1-propene and 1.8 g (14.1 mmol) of N,N-diisopropylethylamine were added, the mixture was stirred at room temperature for 67.9 hours, and then, the reaction solution was purified by a column to obtain 0.03 g of a crude purified product of 5-fluoro-1-(2,4-difluorophenyl)-3-methoxy-4-trifluoromethylpyrazole represented by the following formula (T).

[Formula 26]

(T)

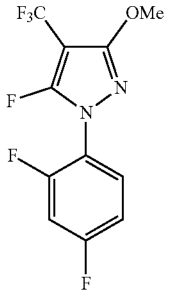

The analysis results of the target product obtained are as follows.

Mass Spectrum (APCI, m/z): 296.8 ($[M]^+$)

$^{19}$F-NMR (400 MHZ, $CDCl_3$) δ ppm: −58.46 (d, J=10.1 Hz, 3F), −107.49−−107.41 (m, 1F), −118.04−−117.92 (m, 1F), −119.55 (q, J=10.1 Hz, 1F)

Example 21

Production of 5-fluoro-1-(pentafluorophenyl)-3-methoxy-4-trifluoromethylpyrazole In 25 ml of acetonitrile, 0.5 g (2.6 mmol) of pentafluorophenylhydrazine hydrochloride was dissolved, and 0.6 g (2.7 mmol) of 1,3,3,3-tetrafluoro-1-methoxy-2-(trifluoromethyl)-1-propene and 1.8 g (13.8 mmol) of N,N-diisopropylethylamine were added, the mixture was stirred at room temperature for 74.3 hours, and then, the reaction solution was purified by a column to obtain 0.07 g of a crude purified product of 5-fluoro-1-(pentafluorophenyl)-3-methoxy-4-trifluoromethylpyrazole represented by the following formula (U).

[Formula 27]

(U)

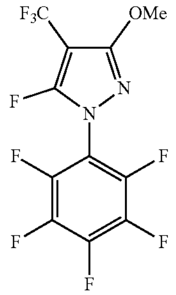

The analysis results of the target product obtained are as follows.

Mass Spectrum (APCI, m/z): 350.1 ($[M]^-$)

$^{19}$F-NMR (400 MHZ, $CDCl_3$) δ ppm: −58.79 (d, J=10.1 Hz, 3F), −119.17 (tq, J=5.8, 10.1 Hz, 1F), −145.58−−145.47 (m, 2F), −150.52 (ddd, J=2.9, 2.9, 21.7 Hz, 1F), −160.90−−160.75 (m, 2F)

Example 22

Production of 5-fluoro-1-[4-(trifluoromethyl)phenyl]-3-methoxy-4-trifluoromethylpyrazole In 28 ml of acetonitrile, 0.5 g (2.9 mmol) of 4-(trifluoromethyl)phenylhydrazine hydrochloride was dissolved, and 0.7 g (3.3 mmol) of 1,3,3,3-tetrafluoro-1-methoxy-2-(trifluoromethyl)-1-propene and 2.1 g (15.9 mmol) of N,N-diisopropylethylamine were added, the mixture was stirred at room temperature for 64.5 hours, and then, the reaction solution was purified by a column to obtain 0.07 g of a crude purified product of 5-fluoro-1-[4-(trifluoromethyl)phenyl]-3-methoxy-4-trifluoromethylpyrazole represented by the following formula (V).

[Formula 28]

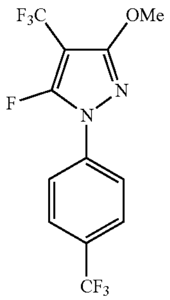

(V)

The analysis results of the target product obtained are as follows.

Mass Spectrum (APCI, m/z): 328.8 ($[M]^+$)

$^{19}$F-NMR (400 MHZ, $CDCl_3$) δ ppm: −58.53 (d, J=10.1 Hz, 3F), −63.74 (s, 3H), −119.30 (q, J=10.1 Hz, 1F)

Example 23

Production of 1-(2,4,6-trichlorophenyl)-5-fluoro-3-methoxy-4-trifluoromethylpyrazole In 24 ml of acetonitrile, 0.5 g (2.9 mmol) of 2,4,6-trichlorophenylhydrazine hydrochloride was dissolved, and about 0.6 g (2.8 mmol) of 1,3,3,3-tetrafluoro-1-methoxy-2-(trifluoromethyl)-1-propene and 1.6 g (12.3 mmol) of N,N-diisopropylethylamine were added, the mixture was stirred at room temperature for 17 days, and then, the reaction solution was purified by a column to obtain a crude purified product of 1-(2,4,6-trichlorophenyl)-5-fluoro-3-methoxy-4-trifluoromethylpyrazole represented by the following formula (W).

[Formula 29]

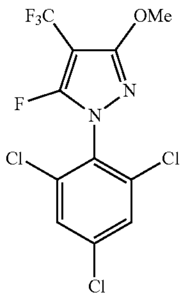

(W)

The analysis results of the target product obtained are as follows.

Mass Spectrum (APCI, m/z): 364.3 ($[M+H]^+$)

Example 24

Production of 1-(3,4-dichlorophenyl)-5-fluoro-3-methoxy-4-trifluoromethylpyrazole In 23 ml of acetonitrile, 0.5 g (2.4 mmol) of 3, 4-dichlorophenylhydrazine hydrochloride was dissolved, and about 0.6 g (2.8 mmol) of 1,3,3,3-tetrafluoro-1-methoxy-2-(trifluoromethyl)-1-propene and 1.6 g (12.3 mmol) of N,N-diisopropylethylamine were added, the mixture was stirred at room temperature for 72 hours, and then, the reaction solution was purified by a column to obtain 0.04 g of a crude purified product of 1-(3,4-dichlorophenyl)-5-fluoro-3-methoxy-4-trifluoromethylpyrazole represented by the following formula (X).

[Formula 30]

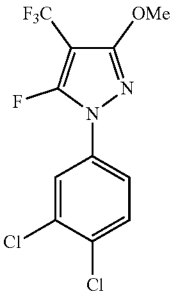

(X)

The analysis results of the target product obtained are as follows.

Mass Spectrum (APCI, m/z): 330.2 ($[M+H]^+$)

$^{19}$F-NMR (400 MHZ, $CDCl_3$) δ ppm: −58.56 (d, J=10.1 Hz, 3F), −119.47 (q, J=10.1 Hz, 1F)

Example 25

Production of 5-fluoro-1-(4-iodophenyl)-3-methoxy-4-trifluoromethylpyrazole

In 21 ml of acetonitrile, 0.5 g (2.2 mmol) of 4-iodophenylhydrazine hydrochloride was dissolved, and 0.5 g (2.4 mmol) of 1,3,3,3-tetrafluoro-1-methoxy-2-(trifluoromethyl)-1-propene and 1.5 g (11.2 mmol) of N,N-diisopropylethylamine were added, the mixture was stirred at room temperature for 17 days, and then, the reaction solution was purified by a column to obtain 0.02 g of a crude purified product of 5-fluoro-1-(4-iodophenyl)-3-methoxy-4-trifluoromethylpyrazole represented by the following formula (Y).

[Formula 31]

(Y)

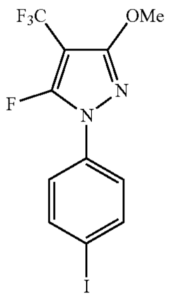

The analysis results of the target product obtained are as follows.

Mass Spectrum (APCI, m/z): 386.2 ([M]$^+$)

$^{19}$F-NMR (400 MHZ, $CDCl_3$) δ ppm: −58.43 (d, J=10.1 Hz, 3F), −120.01 (q, J=10.1 Hz, 1F)

The invention claimed is:

1. A fluorine-containing pyrazole compound represented by the following general formula (1):

[Formula 1]

(1)

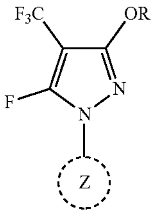

wherein R represents a hydrocarbon group having 1 to 12 carbon atoms; and a ring Z represents a phenyl group having at least one substituent selected from the group consisting of halogen atoms, halogenated alkyl groups, nitro group, alkoxy groups, halogenated alkoxy groups, and sulfonyl groups, or a condensed ring containing no heteroatom as a ring atom.

2. The fluorine-containing pyrazole compound according to claim 1, wherein a number of π electrons constituting the ring Z is 6, 10, 14, 18 or 22.

3. A method for producing a fluorine-containing pyrazole compound, comprising reacting a fluoroisobutylene derivative represented by the following general formula (2) with a compound represented by the following general formula (3) or a salt thereof to obtain a fluorine-containing pyrazole compound represented by the following general formula (1):

[Formula 2]

(2)

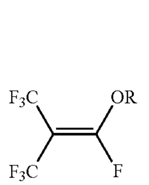

(3)

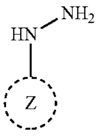

-continued (1)

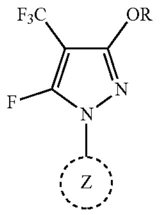

wherein

R represents a hydrocarbon group having 1 to 12 carbon atoms; and a ring Z represents a phenyl group having at least one substituent selected from the group consisting of halogen atoms, halogenated alkyl groups, nitro group, alkoxy groups, halogenated alkoxy groups, and sulfonyl groups, or a condensed ring containing no heteroatom as a ring atom.

4. A method for producing a fluorine-containing pyrazole compound, comprising reacting a fluoroisobutane derivative represented by the following general formula (4) with a compound represented by the following general formula (3) or a salt thereof to obtain a fluorine-containing pyrazole compound represented by the following general formula (1):

[Formula 3]

(4)

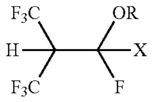

(3)

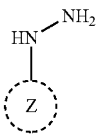

(1)

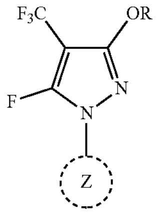

wherein

R represents a hydrocarbon group having 1 to 12 carbon atoms,

X represents a halogen atom, —$OA^1$, —$SO_mA^1$ where m is an integer of 0 to 3, or —$NA^1A^2$, $A^1$ and $A^2$ each independently represent a hydrogen atom or a hydrocarbon group having 1 to 10 carbon atoms, and a ring Z represents a phenyl group having a substituent, or a condensed ring containing no heteroatom as a ring atom.

5. The method for producing a fluorine-containing pyrazole compound according to claim 3, wherein a step of obtaining a fluorine-containing pyrazole compound is carried out in the presence of a fluoride ion scavenger.

6. The method for producing a fluorine-containing pyrazole compound according to claim 3, wherein a number of π electrons constituting the ring Z is 6, 10, 14, 18, or 22.

7. The method for producing a fluorine-containing pyrazole compound according to claim 4, wherein a step of obtaining a fluorine-containing pyrazole compound is carried out in the presence of a fluoride ion scavenger.

8. The method for producing a fluorine-containing pyrazole compound according to claim 4, wherein a number of π electrons constituting the ring Z is 6, 10, 14, 18, or 22.

9. The method for producing a fluorine-containing pyrazole compound according to claim 5, wherein a number of π electrons constituting the ring Z is 6, 10, 14, 18, or 22.

10. The method for producing a fluorine-containing pyrazole compound according to claim 7, wherein a number of π electrons constituting the ring Z is 6, 10, 14, 18, or 22.

* * * * *